United States Patent [19]

Sugimoto et al.

[11] Patent Number: 4,992,374

[45] Date of Patent: Feb. 12, 1991

[54] MUTANT VACCINIA VIRUS AND PROCESS FOR PRODUCTION THEREOF

[75] Inventors: Masanobu Sugimoto, Shiki; Fukumi Nishimaki, Iruma; Tadashi Maruyama; Keizaburo Miki, both of Tokyo; Michio Morita, Chiba; Kazuyoshi Suzuki, Ichikawa, all of Japan

[73] Assignees: Toa Nenryo Kogyo Kabushiki Kaisha, Tokyo; Chiba Prefecture, Chiba, both of Japan

[21] Appl. No.: 79,680

[22] Filed: Jul. 30, 1987

[30] Foreign Application Priority Data

Jul. 31, 1986 [JP] Japan .................. 61-178924

[51] Int. Cl.$^5$ .................. C12N 7/00; C12N 15/00; A61K 39/12
[52] U.S. Cl. .................. 435/235.1; 424/89; 435/240.2
[58] Field of Search .............. 434/235, 89; 435/172.3, 435/320, 240.1, 240.2, 68, 70

[56] References Cited

FOREIGN PATENT DOCUMENTS 0110385 6/1984 European Pat. Off. .
0157528 10/1985 European Pat. Off. .

OTHER PUBLICATIONS

Takahashi-Nishmaki, et al., *J. Gen. Virol.* 68:2705-2710 1987.
Shida, et al., J of Virology, 62:4474-4480, 1988.
Proc. of Nat'l Acad. Sci. U.S.A., vol. 82, May 1985, pp. 3365-3369.
Nature, vol. 317, Oct. 31, 1985, No. 67262.
Biol. Abstracts, vol. 83, 1987, No. 107689.
M. Sugimoto et al., Microbiol. Immunol. vol. 29(5), 421-428, 1985 S. Hashizume, Vaccinia Viruses as Vectors for Vaccin Antigens, 87-99, 1985.

*Primary Examiner*—Robin L. Teskin
*Assistant Examiner*—Beth A. Burrous
*Attorney, Agent, or Firm*—Michael N. Meller

[57] ABSTRACT

An improved mutant vaccinia virus providing a pock and plaque size on RK13 cells that is approximately the same as those of the Lister original, having a proliferation potency on YTV cells that is approximately the same as that of the Lister original, and having a neurovirulence, assessed by a recovery of an intrabrain virus, that is lower than that of the Lister original; and a process for the production thereof.

1 Claim, 4 Drawing Sheets

Fig. 1a

MUTANT VACCINIA VIRUS AND PROCESS FOR PRODUCTION THEREOF

BACKGROUND OF THE INVENTION

1. Field of the Invention

The present invention relates to an improved mutant vaccinia virus and a process for the production thereof.

2. Description of the Related Art

The vaccinia virus was originally developed as a vaccination virus. Recently, however, vaccinia virus has drawn attention as a vector for a recombinant technique, a gene coding for an antigenic protein of a particular pathogenic virus, i.e., exogenous antigen gene, is introduced into a vaccinia virus gene as a vector for the construction of a recombinant vaccinia virus. According to this technique, the development of a vaccine against viral disease, which has been difficult so far, can be realized. Therefore, the vaccinia virus has become useful as a vector virus for the construction of a recombinant vaccinia virus.

A virus for a vaccine must have both a high proliferation potency and a low toxicity (pathogenic potency?), especially neurovirulence. Therefore, to obtain a recombinant vaccina virus by introducing an exogenous antigen gene into a vector vaccinia virus, the vector vaccinia virus per se. must have the above-mentioned desired properties.

The Lister original (LO) strain of the vaccination virus has a high proliferation potency, but at the same time a ralatively high neurovirulence, which is disadvantageous as the vaccination virus and as the vector for the construction of a recombinant virus as a vaccine. As an improved vaccination virus which does not have this disadvantage, a mutant Lister clone 16 (LC16) has been from the Lister original (LO) strain (Hashisum et al. Vacinia Viruses as Vectors for Vaccine Antigens, Elsevier, 1985, p 87–99).

The above-mentioned LC16 was passaged six times on RK cells and cloned by a plaque method to obtain a mutant LC16m0 strain which provides relatively small and even-size pocks on a chorio-allantoic membrane. The mutant LC16m0 was further passaged three times and recloned to isolate an LC16m8 strain, which exhibits a very small pock size. The LC16m8 is advantageous as a vaccination virus in that it has a low neurovirulence, a low proliferation potency in the brian, a low invasion potency, a low recovery of virus from virus inoculated brain, and provides a good histopathlogical feature of the brain after inoculation of virus. However, the LC16m8 is disadvantageous in that it has a low proliferation potency in the skin and a low in vitro proliferation on Vero cells (Hashizume, *Rinsho To Virus*, Vol 3, No. 3, 225–235, 1975).

The gene structures of the original LO strain and the mutant LC16m8 strain were compared, and it was found that a Hind III D fragment of about 10 kb derived from the LC16m8 carries an Xho I site, although a corresponding fragment derived from the LO does not carries the Hind III site, suggesting that genes related to the proliferation and neurotoxicity of virus are present on the Hind III D fragment (Sugimoto et al., *Microbiol. Immunol.* Vol 29 (5), 401–428, 1985).

As seen from above, although a vaccinia virus which has a high proliferation potency and high pathogenic properties, and a vaccinia virus which has a low proliferation potency and low pathogenic properties, including neurotoxicity, are known, a vaccinia virus possessing a high proliferation potency with a low pathogenic properties is not known.

SUMMARY OF THE INVENTION

The present invention provides a vaccinia virus which has both a high proliferation potency and low pathogenic properties, especially a low neurovirulence, and therefore, is useful as a vector for the construction of various recombinant virus vaccines.

More specifically, the present invention provides an improved mutant vaccinia virus comprising, a parent mutant vaccinia virus derived from a vaccinia virus Lister original wherein at least a part of a Hind III DNA D fragment region of the parent mutant vaccinia virus gene has been replaced by at least a corresponding part of a Hind III D fragment of the vaccinia virus Lister original gene, wherein the parent mutant vaccinia virus provides a pock size and plaque size on RK13 cells smaller than those provided by the Lister original, has a proliferation potency on YTV cells lower than that of the Lister original, and has a neurovirulence, assessed by a recovery of an intrabrain virus, lower than that of the Lister original, and wherein the improved mutant vaccinia virus provides a pock size and plaque size on RK13 cells that is approximately the same as those of the Lister original, has a proliferation potency on YTV cells that is approximately the same as that of the Lister original, and has a neurovirulence, assessed by a recovery of an intrabrain virus, lower than that of the Lister original.

The present invention also provides a process for the production of an improved mutant vaccinia virus, comprising the steps of:

preparing a parent mutant vaccinia virus derived from a vaccinia virus Lister original, wherein the parent mutant vaccinia virus provides a pock size and plaque size on RK13 cells smaller than those provided by the Lister original, has a proliferation potency on YTV cells lower than that of the LIster original, and has a neurovirulence, assessed by a recovery of an intrabrain virus, lower than that of the Lister original;

preparing a Hind III D fragment from the Lister original gene;

replacing at least a part of the Hind III D fragment region of the parent mutant vaccinia virus gene by at least a part of the Hind III D fragment of the Lister original gene; and selecting an improved mutant vaccinia virus providing a pock size and plaque size on RK13 cells that is approximately the same as those of the Lister original, having a proliferation potency of YTV cells that is approximately the same as that of the Lister original, and having a neurovirulence, assessed by a recovery of an intrabrain virus, lower than that of the Lister original.

BRIEF DESCRIPTION OF THE DRAWINGS

FIG. 1a is a sketch of electrophoresis patterns of Xho I digestion fragments derived from genes of parent vaccinia virus strains LO and mutant LO16m8, as well as mutant strains LOTC-1, LOTC-2, LOTC-3, LOTC-4 and LOTC-5 of the present invention. In these digestion patterns, digestion fragments from each strain are designated as A, B, C, D ... according to the size of each fragment; and FIG. 1b is a photograph corresponding to a part of the sketch of FIG. 1a;

DESCRIPTION OF THE PREFERRED EMBODIMENT

An improved mutant vaccinia virus of the present invention can be obtained by replacing a part of or the entire Hind III D region in a parent mutant virus with a corresponding Hind III D region derived from an LO viral gene.

(1) PARENT MUTANT STRAIN

The parent mutant virus is a viral strain which is used as a parent, i.e., a starting virus, for the construction of an improved mutant virus of the present invention, but is a mutant derived from an original strain LO. These parent mutant viruses have a low proliferation potency and low pathogenic properties, and are exemplified by an LC16 series strains. The process for the construction and the properties of these parent mutant viruses are disclosed in detail in *Rinsho To Virus,* Vol 3, No. 3, 229–235, 1975. These mutant viruses are available from Chiba Serum Institute, Japan. The properties of the preferable parent mutant LC16m8 are compared with those of the original LO in Table 1.

TABLE 1

| Virus strain | LO | LC16m8 |
|---|---|---|
| Temperature at which virus cannot proliferate on RK cells | >41° C. | 40.5° C. |
| Plaque size on RK cells | Large | Medium |
| Pock size | Large | Small |
| Proliferation potency on | | |
| CAM | +++ | +++ |
| Vero cells | +++ | + |
| RK cells | +++ | +++ |
| CEF cells | ++ | ++ |
| Neurovirulence to central nervous system | | |
| Proliferation | | |
| Rabbit | ++ | ± |
| Monkey | +++ | + |
| Mouse | + | |
| Invasion | | |
| Mouse | +++ | − |
| Proliferation in skin | | |
| Rabbit | +++ | + |
| Human | ++ | + |
| Antibody productivity | | |
| Rabbit | ++ | ++ |
| Human | ++ | ++ |

(2) CONSTRUCTION OF IMPROVED MUTANT VIRUS STRAINS

The construction process of the improved mutant virus strains of the present invention is described with the use of an LC16m8 strain as a parent mutant virus.

First, a Hind III D fragment of the LO virus DNA was prepared as follows: virion of the LO strain were prepared by as follows: Viruses were proliferated in RK13 cells. After freezing and thawing of the cultured cells, cell debris was removed by centrifugation. Virion were collected by the ultracentrifugation of the supernatant. Virion were then purified by sucrose density ultracentrifugation. The virion were treated with a phosphate buffer (pH 6.8) containing 1% of a surfactant Sarkosyl NL97 and 6M of urea to extract the DNA according to Juklik, W. K., *Biochem. Biophys. Acta,* 61, 290–301, 1962. The DNA preparation was extracted with phenol/chloroform to eliminate proteins, and the purified DNA was digested with 10 units of Sma I in 10 μl of a buffer containing 10 mM Tris-HCl (pH 7.5), 7 mM $MgCl_2$, 20 mM KCl, 7 mM 2-mercaptoethanol and 100 μg/ml bovine serum albumin at 30° C. for 1 hour. As a result the DNA was cleaved into a large fragment A and a small fragment B. The fragment B (1 μg) was further digested with 10 units of Hind III in 10 μl of a buffer containing 10 mM Tris-HCl (pH 8.0), 7 mM $MgCl_2$, 10 mM NaCl and 100 μg/ml bovine serum albumin at 37° C. for 1 hour. The resulting fragments were cloned in plasmid pUC9 as follows.

The Hind III digests were extracted with phenol followed by phenol-chloroform-isoamylalchol, and precipitated with ethanol. Recovered DNA was ligated with 10 units of T4 CNA ligase in 50 mM Tris-HCl (pH 7.6), 6.6 mM $MgCl_2$, 10 mM dithiothreitol, 66 μM ATP into pUC9 which had been digested with Hind III. *E. coli* (M109) was transformed with the ligated plasmid. White colonies containing the plasmid with foreign gone were selected. A clone containing a plasmid containing a DNA fragment of about 10 kb was selected as follows. DNA was extracted from the transformed *E. Coli* (JM109) according to boiling method (Molecular Cloning, T. Maniatis et al., Cold Spring Harbor Laboratory, 1982, pp 366–369. DNA was digested with a restriction enzyme Hind III, and the resultant DNA fragment was separated by agarose electropholesis. The plasmids producing about 10 kb flagment were cloned. It was confirmed by the Southern blotting method that the DNA fragment of about 10 kb was a Hind D III fragment. That is, this DNA fragment migrated to the same position as that of the Hind III D fragment prepared by digesting an LO virus gene directly with the Hind III in electrophoresis and hybridized with an Xho B fragment (Sugimoto et al., Microbiol. Immunol. 29, 420, 1985).

The Hind III D fragment thus obtained from the LO virus gene was transfected to the LC16m8 virus gene as follows: RK13 cells were inoculated into a culture bottle containing 5 ml of RPM1640 containing 10% fetal bovine serum, having a culture surface of 25 cm to form a monolayer, and a $10^5$PFU/bottle (about 0.1 PFU/cell) of the LC16m8 virus was infected to the cultured cells. Next, the above-mentioned Hind III D fragment preparation derived from the LO strain was added to the infected monolayer by the calcium phosphate method. 2 μg of the plasmid containing the Hind III D fragment with 20 μg of calf-thymus DNA as a carrier in 0.24 M $CaCl_2$ solution (2.5 ml) was mixed by drop with bubbling of air to the solution containing 2.5 ml of 2×HBS (10 g HEPES and 6 g NaCl/1, pH 7.10) and 0.05 ml 100 $PO_4$(70 mM $NaH_2PO_4$ and 70 mM $NaHPO_4$). The solution was stood for 30 min. The solution with precipitated DNA with calcium phosphate was added to RK 13 cell culture infected withe LC16m8. After six hours, the culture medium was exchanged and culturing was carried out for 48 hours at 37° C. The cultured broth was subjected to repeated freezing and thawing to recover a virus, and a 5 ml/bottle of virus solution was obtained. The virus in this solution was then titrated.

Next, viruses subjected to the recombination treatment described above were screened to select virus strains forming a large plaque, as follows: RK13 cells were inoculated into a plastic petri dish having a diameter of 6 cm and containing 5 ml of a PBR1640 medium with 10% fetal bovine serum, and cultured for 24 hours at 37° C. to form a monolayer. 0.1 ml of 1/10 to 1/100 — dibuted above-prepared virus solution was added to the monolayer, and the cultured cells adsorbed the virus. 3 ml of Eagle's MEM medium containing 1% agar and 10% bovine serum was layered over the monolayer according to a conventional method, and culturing was carried out for three days at 37° C. In this manner, a virus which forms large plaques having a diameter of about 3 to 4 mm was obtained. The above-mentioned cloning procedure was repeated three times to clone the desired virus strains.

These virus strains formed large plaques generated at a ratio of 4 to 8 per 100PFU of starting virus. Since the LC16m8 strain does not form large plaque on RK13 cells and there is little possibility of the occurrence of a spontaneous mutation providing mutants at a high ratio as described above, it is believed that most of the virus strains forming large plaques are generated by a recombination between the Hind III D regions of the LO virus gene and the LC16m8 virus gene.

Five typical virus strains, i.e., LOTC-1, LOTC-2, LOTC-3, LOTC-4, and LOTC-5, were selected, cloned and further characterized.

(3) DNA ANALYSIS

Figure 1A:
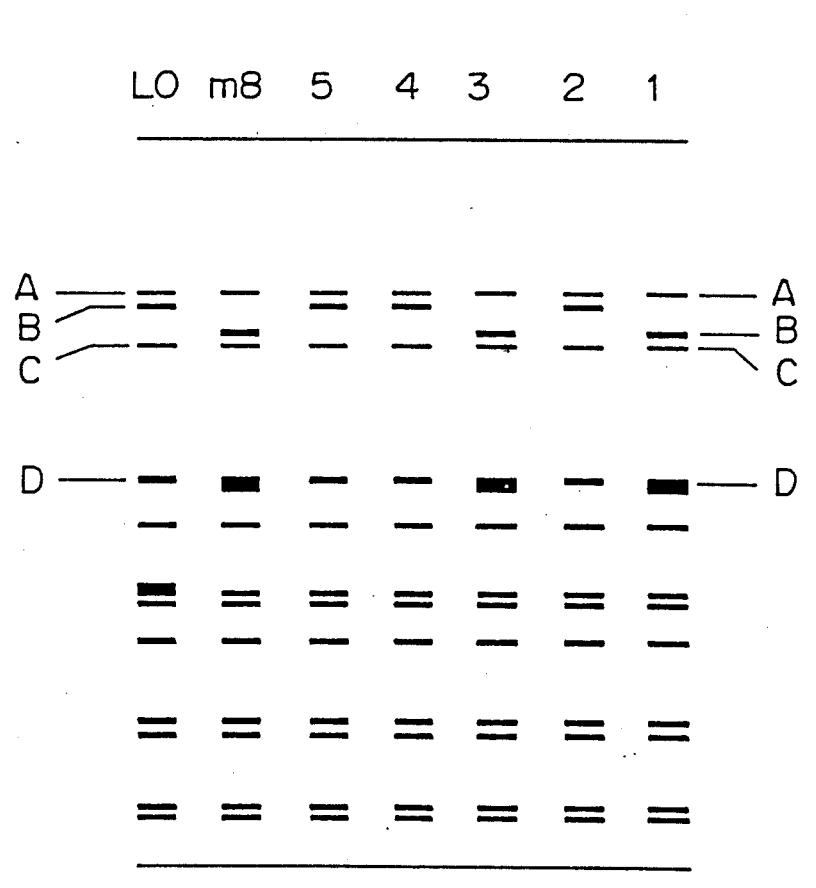
Figure 1B:
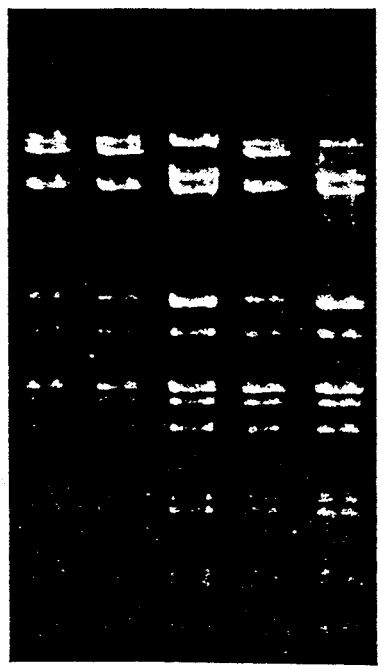

DNAs were extracted from the LO strains, LC16m8 strain, and the above-mentioned five strains of the present invention according to a conventional method, digested with a restriction enzyme Xho I, and the digestion product was analyzed by agarose gel electrophoresis. The separation patterns are shown in FIGS. 1a and 1b.

As seen from FIG. 1, the size of the B fragment of the LC16m8 strain is smaller than that of the B fragment of the LO strain. However, the LC16m8 strain provides an extra D fragment which is not derived from the LO strain. This means that the Hind III D fragment contains an XhoI site which is not present at the corresponding site of the LO virus gene. Among the improved mutant strains of the present invention, LOTC-2, LOTC-4 and LOTC-5 provide the same digestion pattern as that of the LO strain, revealing that the recombination occurred at region encompassing the Xho I site in question. However, the LOTC-1 and LOTC-3 strains provide the same digestion pattern as that of the LC16m8 strain, revealing that the recombination occurs at an region other than the Xho I site.

Figure 2:
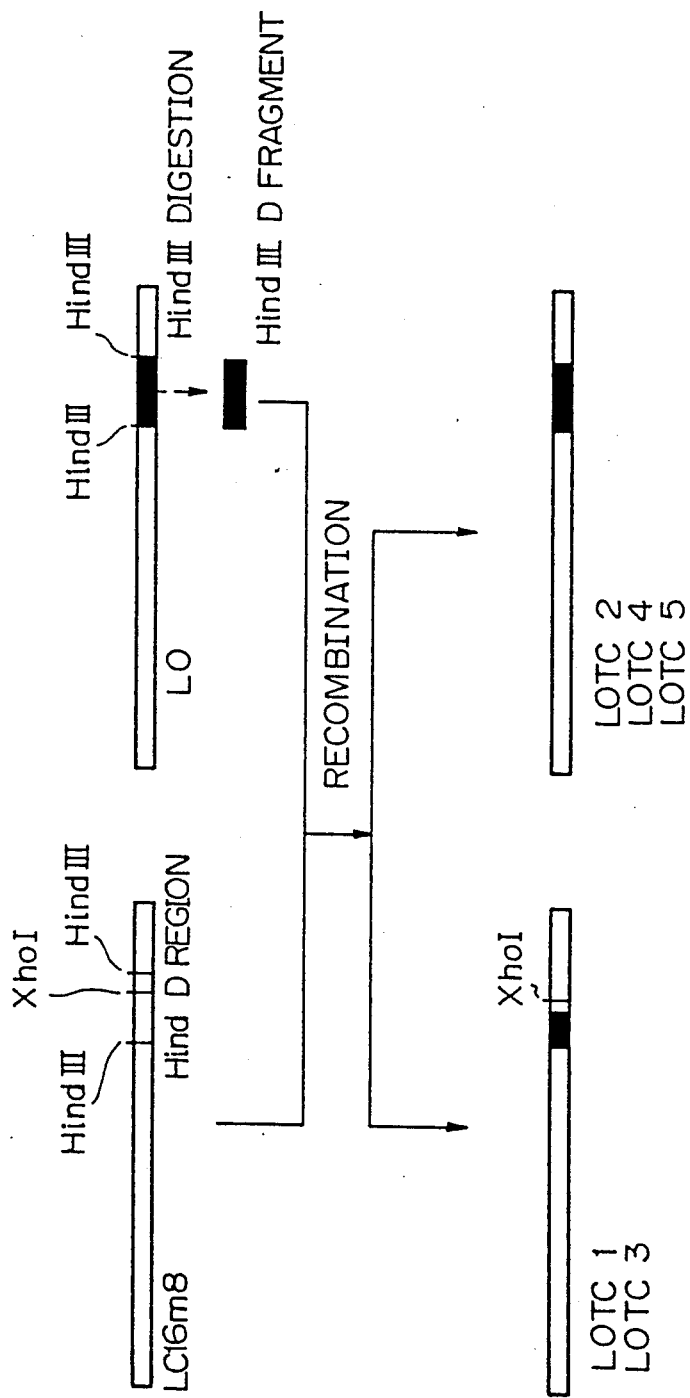
FIG. 2 schematically represents a process of recombination between a gene fragment derived from a parent LO strain and a gene fragment of a parent mutant LC16m8 strain to form a recombinant gene, wherein a Hind III D fragment of the LC16m8 strain genome is replaced with a corresponding fragment of the LO strain; and, FIG. 3 is a photograph comparing the size of plaque of the parent strains LO and LC16m8 as well as the LOTC-1 to LOTC-5 of the present invention.

Taking the above-mentioned result into consideration, the process of the recombination is schematically shown in FIG. 2.

(4) CHARACTERIZATION OF IMPROVED MUTANT VIRUS STRAINS

The properties of the LOTC series mutant strains are summarized in comparison with the LO and LC16m8 strains, as follows.

a) Neurovirulence

Each of the above-mentioned virus was inoculated into the brain of a rabbit at an amount of $10^{6.8}$ of $TCID_{50}$, and six days later, the rabbit was killed and the neurovirulence was assessed. A WR strain (++), LO strain (+), LC16m0 strain (±), and LC16m8 (−) strains were used as controls. The results showed that the LOTC-3 and LTC-5 strains were no less toxic than the LC16m8, and the LOTC-1, LOTC-2 and LOTC-4 strains were less toxic than the LC16m0. These results are shown in Table 2.

TABLE 2

| Virus strain | Recovery at sixth day ($log_{10}TCID_{50}/ml$) | Assessment by recovery |
|---|---|---|
| LOTC-1 | <0.5, 2.5 | ± |
| LOTC-2 | <0.5, 1.25, 1.75, 2.0 | + |
| LOTC-3 | <0.5, <0.5, <0.5, <0.5 | − |
| LOTC-4 | <0.5, 3.0 | ± |
| LOTC-5 | <0.5, <0.5 | − |
| LO | 2.5, 3.5, 3.75, 4.75 | ++ |
| LC16m8 | <0.5, <0.5, <0.5 | − |
| LC16m0 | <0.5, <0.5, 4.25 | + |
| WR | 5.75, 6.5, 7.0 | +++ |

(b) In vitro virus proliferation (i) Plaque size on RK13 cells

Figure 3:

As shown in FIG. 3, plaques of the LO strain are very much larger than those of the LC16m8, and the plaques of the LOTC-1 to LOTC-5 strains are similar in size to those of the LO strain.

(ii) Proliferation on YTV (Vero cells)

Although the LC16m8 strain makes small plaques but can proliferate on RK13 cells, this LC16m8 strain has a very poor proliferation on YTV cells. Accordingly, the RK13/YTV ratio in plaque number is as high as about 500. Conversely, the LO strain is highly proliferate on YTV cells, and accordingly, the RK13/YTV ratio is less than 1. the RK13/YTV ratios of the LOTC-1 to LOTC-5 strains of the present invention are similar to that of the LO strains. The results are shown in Table 3.

(iii) Pock size

The pock size of the LC16m8 strain observed on a fertilized hen's egg is small, and that of the LO strain is large. These pock sizes of the LOTC series strains of the present invention were medium to large, and those of the LOTC strains not having the Xho I site in the recombination region in question were larger than those of the LOTC strains having the Xho I site. The results are shown in Table 3.

TABLE 3

| Virus strain | Proliferation property RK13/YTV | Plaque size on RK13 cells | Pock size |
|---|---|---|---|
| LO | 0.22 | Large | Large |
| LC16m8 | 500 | Small | Small |
| LOTC-1 | 0.91 | Large | Medium |
| LOTC-2 | 0.88 | Large | Large |
| LOTC-3 | 0.71 | Large | Large |
| LOTC-4 | 0.88 | Large | Large |
| LOTC-5 | 1.15 | Large | Large |

As seen from the above-mentioned characteristics of the mutant virus strains of the present invention, the present invention provides improved mutant virus strains and a process for the production thereof. The present mutant virus strains have a proliferation potency as high as that of the LO strain, and a neurovirulence lower than that of the LO strain.

These mutant virus strains are promising as attenuated vaccination viruses as well as vectors for the construction of a recombinant vaccinia virus.

LOTC-5 has been deposited under the Budapest Treaty in the Pasteur Institute with a deposit number I-953 on May 30, 1990.

We claim:

1. An improved mutant vaccinia virus which is LOTC-5.

* * * * *